United States Patent [19]

Goudie

[11] 4,299,844
[45] Nov. 10, 1981

[54] 2-ACYLOXY-4-(6-SUBSTITUTED-2-NAPH-THYL)BUTANES

[75] Inventor: Alexander C. Goudie, Harlow, England

[73] Assignee: Beecham Group Limited, England

[21] Appl. No.: 55,613

[22] Filed: Jul. 9, 1979

Related U.S. Application Data

[63] Continuation of Ser. No. 792,724, May 2, 1977, abandoned.

[30] Foreign Application Priority Data

May 13, 1976 [GB] United Kingdom ............... 19653/76
Oct. 1, 1976 [GB] United Kingdom ............... 40937/76

[51] Int. Cl.$^3$ .................... C07C 69/14; C07C 69/614; C07C 69/78; C07C 69/92
[52] U.S. Cl. .................................. 424/308; 260/463; 424/301; 424/311; 549/22; 560/66; 560/72; 560/105; 560/107; 560/173; 560/185; 560/187; 560/255

[58] Field of Search ............... 560/255, 173, 107, 105, 560/187, 72; 424/311, 308

[56] References Cited

U.S. PATENT DOCUMENTS 4,035,406 12/1977 Anderson et al. .................. 560/255

FOREIGN PATENT DOCUMENTS 819794 2/1975 Belgium ............................ 560/255

Primary Examiner—Howard T. Mars
Assistant Examiner—Michael Shippen
Attorney, Agent, or Firm—Jacobs & Jacobs

[57] ABSTRACT

Anti-inflammatory naphthyl compounds, their preparation and pharmaceutical compositions containing the same. The anti-inflammatory activity has a wide spectrum coupled with low side effects such as gastrointestinal irritancy or oestrongenicity. The compounds possess a chiral center at C-2 and can exist as mixtures of optical isomers or as substantially pure optical isomers.

5 Claims, No Drawings

2-ACYLOXY-4-(6-SUBSTITUTED-2-NAPHTHYL)-BUTANES

CROSS-REFERENCE

This is a continuation, of Ser. No. 792,724 filed May 2, 1977 now abandoned.

The present invention provides naphthyl derivatives, a process for their preparation and compositions containing them.

Belgian Pat. No. 219794 and British Pat. No. 1474377 disclose inter alia the compounds of the formula (I):

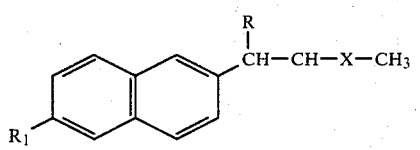

wherein X is CO or CHOH; R is H or $CH_3$; $R_1$ is a chlorine or bromine atom or a methoxyl, methylthio or $C_{1-4}$ alkyl group; and the dotted line represents an optional double bond. The compounds were stated to have a good degree of anti-inflammatory activity. A distinct group of novel naphthyl compounds has now been found which have a broad spectrum of anti-inflammatory activity coupled with a low level of such side effects as gastro intestinal irritancy or oestrogenicity.

The present invention provides the compounds of the formula (II):

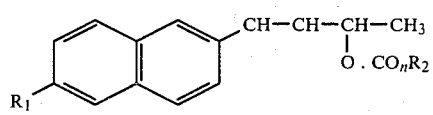

wherein $R_1$ is a chlorine or bromine atom or a methoxyl, methylthio or $C_{1-4}$ alkyl group; n is 1 or 2; the dotted line represents a double bond optionally present; and $R_2$ is an organic group such that $R_2CO_2H$ is a pharmaceutically acceptable acid of up to 12 carbon atoms.

One suitable group of the compounds of the formula (II) is that of the formula (III) wherein $R_1$ and $R_2$ are defined as in relation to formula (II) but a more suitable group of compounds owing to their greater freedom from side effects is that of the formula (IV) wherein $R_1$ and $R_2$ are as defined in relation to formula (II):

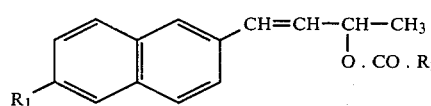

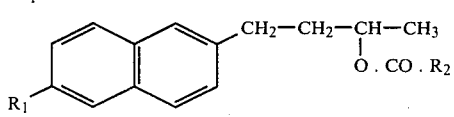

Particularly suitable values for $R_1$ in the compounds of the formulae (II), (III) and (IV) include the chlorine atom and the methyl, methoxy and methylthio groups.

A preferred value for $R_1$ in the compounds of the formulae (II), (III) and (IV) is the methoxyl group.

Particularly favoured compounds of this invention include those of the formula (IV) wherein $R_1$ is a methoxyl group.

Suitably $R_2$ is a hydrocarbon group such as an alkyl, alkenyl, aryl, aralkyl or like group optionally substituted by alkoxyl, carboxyl, carboxamido, hydroxyl, acyloxy, amino, or salted amino, acylamino, alkylamino, dialkylamino or the like. More suitably $R_2$ is such a group which contains up to 8 carbon atoms.

Preferred groups $R_2$ include the phenyl group, alkyl groups of 1-4 carbon atoms, alkyl group of 1-4 carbon atoms substituted by a phenyl group, or one of these groups substituted by hydroxyl, acetoxyl, methoxyl, acetamido, amino, salted amino, lower alkylamino, di-lower alkylamino, carboxyl or the like groups.

Particularly suitable groups $R_2$ include the methyl, ethyl, n-propyl, iso-propyl, n-butyl, t-butyl, phenyl, benzyl, phenylethyl, acetoxymethyl, methoxymethyl, hydroxymethyl, aminomethyl, 2-acetoxyphenyl, 4-methoxyphenyl, 3,4-dimethoxyphenyl, 3,4,5-trimethoxyphenyl or the like groups.

Preferred groups $R_2$ include the methyl, ethyl, benzyl, 2-methoxyethyl, phenyl, 4-methoxyphenyl, salted aminomethyl and the like and particularly the methyl, ethyl, phenyl, or like groups such as 2-acetoxyphenyl.

The compounds of the formulae (II), (III) and (IV) possess a chiral centre at C-2. The compounds of this invention are envisaged as mixtures of optical isomers and in the form of substantially pure optical isomers. The S-isomers of the compounds of the formulae (II), (III) and (IV) form a favoured aspect of this invention especially the S-isomers of the compounds of the formula (IV) wherein $R_1$ is a methoxyl group since the relevant intermediates are readily available by the processes described herein.

The present invention also provides a pharmaceutical composition which comprises a compound of the invention together with a pharmaceutically acceptable carrier.

Most suitably the compositions of this invention are adapted for oral administration although compositions adapted for other modes of administration, such as injection, are also envisaged.

The compositions of this invention may contain conventional carriers such as disintegrants, lubricants, binders, flavours or any other conventional excipient such as those known to be useful in formulating such conventional anti-inflammatory agents as naproxen, ketoprofen, acetylsalicylic acid, indomethacin or the like.

In general the compositions of this invention are provided in unit dosage forms such as tablets, capsules, sachets and their equivalents. Unit dosage compositions will normally contain from 25 mg to 500 mg of active agent, and more usually from 50 mg to 250 mgs of active agent. Such compositions may be taken one or more times a day, usually 1 to 6 times daily and more usually 2, 3 or 4 times a day. The daily dosage of active agent will normally be in the range 200 mg to 1200 mgs for a 70 kg adult.

The present invention also provides a process for the preparation of the compounds of the formula (II) which process comprises the reaction of a compound of the formula (V):

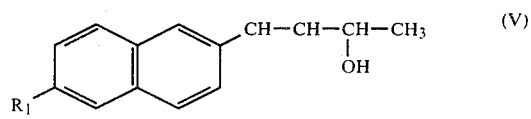

wherein $R_1$ and the dotted line are as defined in relation to formula (II); with a compound of the formula (VI):

$$R_2.O_n C.OH \qquad (VI)$$

or a reactive acylating derivative thereof wherein $R_2$ and n are as defined in relation to formula (II).

Suitable reactive acylating derivatives of the acid of the formula (VI) include acid halides such as the acid chloride, acid anhydrides, mixed anhydrides, active esters or other conventional acylating agents such as the derivatives formed by the reaction of the acid (VI) with a dehydrating agent such as dicyclohexylcarbodiimide.

If the group $R_2$ contains an acylatable group such as an amino or hydroxyl group then it should be protected during the reaction in conventional manner for example by protonation or silylation or the like.

The acylation will normally be carried out in a conventional organic solvent such as tetrahydrofuran, dioxane, methylene chloride, chloroform, pyridine or toluene. If a non-basic solvent is employed then an acid acceptor such as pyridine, triethylamine or the like should be present during the reaction.

The acylation reaction will normally be carried out at a non-extreme temperature, for example $-10°$ to $100°$ C. and more usually at about $0°-25°$ C. It is frequently very convenient to carry out the reaction at ambient temperature.

If the compound of the formula (V) is a mixture of isomers then the compound of the formula (II) prepared by this process will normally be produced as a mixture of isomers. Similarly if the compound of the formula (V) employed is in the form of a pure optical isomer such as the S-isomer than the compound of the formula (II) produced by the process will also be in the form of the pure optical isomer such as the S-isomer.

The novel S-isomers of the formula (V) are useful intermediates and as such form a part of this invention. Most suitably such S-isomers of the compounds of the formula (V) are those wherein the dotted line does not represent a double bond.

EXAMPLE 1

2-Acetoxy-4-(6-methoxy-2-naphthyl)butane

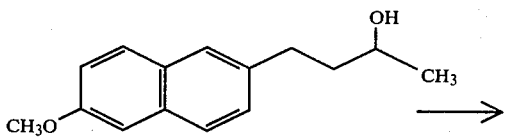

To a solution of 4-(6-methoxy-2-naphthyl)-butan-2-ol (1.5 g; 0.005 mole) in dry pyridine was added acetyl chloride (1.4 g; 0.02 mole) dropwise at 0° C. The resulting solution solidified and a little dry benzene was added and the solution left stirring overnight.

The solution was poured into water and extracted into benzene, dried and evaporated.

The resulting oil was passed down an alumina column and eluted with 60°-80° petrol/ether and the pure acetyl compound was obtained in about 85% yield as a colourless oil. Analysis: $C_{17}H_{20}O_3$ (Requires C=74.97, H7.40) Found C=74.97, H=7.43

The butanol was prepared as follows:

To a stirred solution of 4-(6'-methoxy-2'-naphthyl)butan-2-one (5 g) in ethanol (500 ml) at 5° C. was added sodium borohydride (1 g)portionwise. After a further 3 hours at room temperature the mixture was treated carefully with aqueous ammonium chloride, concentrated and extracted several times with diethyl ether. The organic extract was washed with water, dried ($Na_2SO_4$) and concentrated to give 4-(6-methoxy-2-naphthyl)butan-2-ol, m.p. 94°-5° C. (4.7 g). 2-Acetoxy-4-(6-methoxy-2-naphthyl)butane has been shown to be active on the rat carageenin model at 45 mg/kg per oral and active on the rat cotton pellet test at 50 mg/kg per oral indicating that the compound has good anti-inflammatory activity. No gastric irritation has been observed at doses up to 100 mg/kg per os and no deaths in test animals have been observed during testing.

EXAMPLE 2

2-Acetoxy-4-(6-methoxy-2-naphthyl)but-3-ene

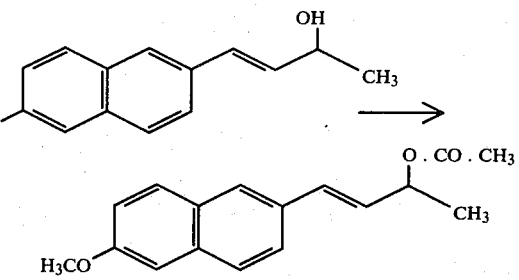

In a similar manner to Example 1, reduction of 4-(6-methoxy-2-naphthyl)but-3-en-2-one with sodium borohydride in ethanol gave 4-(6-methoxy-2-naphthyl)but-3-en-2-ol, m.p. 123°-5° C., which was acetylated as in Example 1 to give 2-acetoxy-4-(6-methoxy-2-naphthyl)-but-3-ene, m.p. 78°-80° C.

The above compound was found to be active on the rat cotton pellet test at 50 mg/kg.

EXAMPLE 3

Hydrogen 3,3-dimethylglutarate of 2-hydroxy-4-(6-methoxy-2-naphthyl)butane

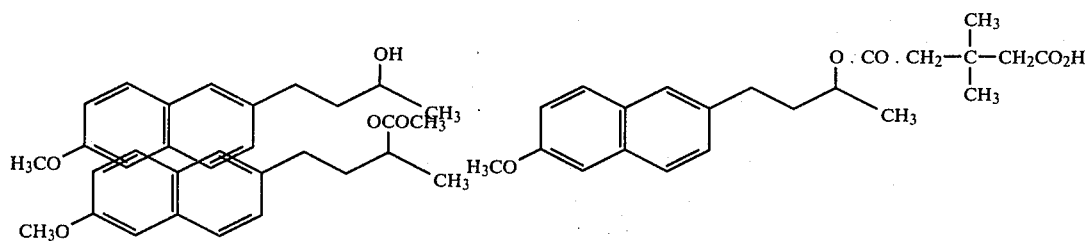

A mixture of 2-hydroxy-4-(6-methoxy-2-naphthyl)butane (2.3 g: 0.01 mole), 3,3-dimethyl glutaric anhydride (1.56 g: 0.011 mole), pyridine (3 ml) and toluene (50 ml) was refluxed for 48 hours. The resulting solution was concentrated, partitioned between ether and water and the organic layer extracted with dilute aqueous sodium hydroxide. These extracts were washed with ether and acidified with dilute hydrochloric acid. The solid which precipitated was collected by filtration and recrystallised from chloroform/hexane to afford the hydrogen 3,3-dimethylglutarate of 2-hydroxy-4-(6'-methoxy-2'-naphthyl)butane, m.p. 85°–6° (2 g).

EXAMPLE 4

3,4,5-Trimethoxybenzoate of 2-hydroxy-4-(6-methoxy-2-naphthyl)butane

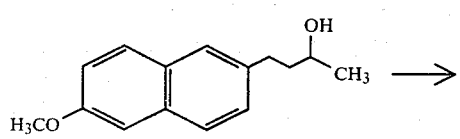 →

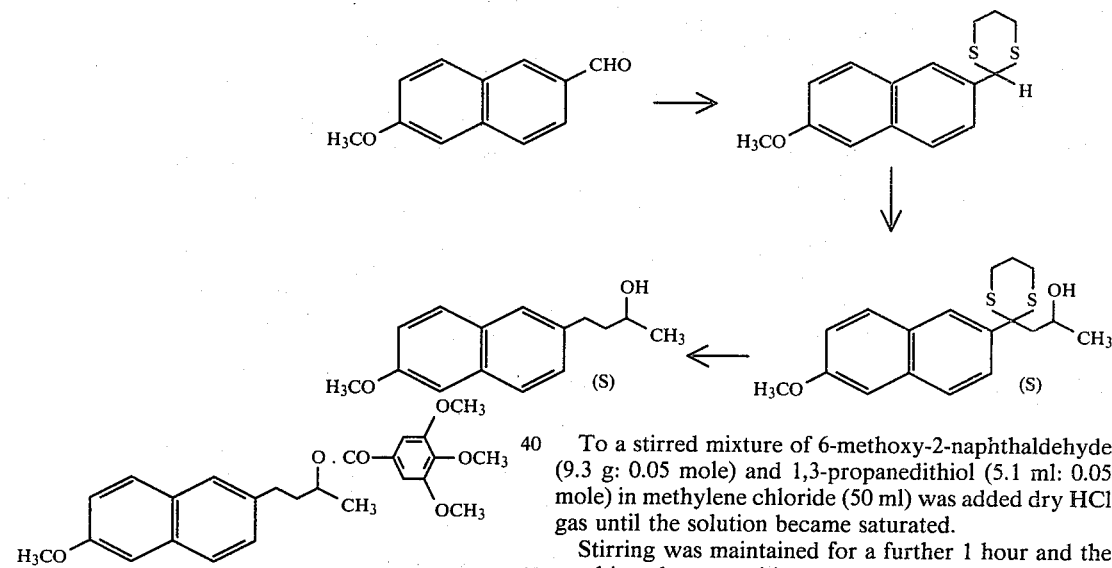

To a stirred mixture of 2-hydroxy-4-(6-methoxy-2-naphthyl)butane (1.15 g: 0.005 mole) in toluene (45 ml) containing dry pyridine (3 ml) was added 3,4,5-trimethoxy-benzoyl chloride, prepared from the corresponding acid (1.06 g: 0.005 mole) and oxalyl chloride (1 ml). After standing for 48 hours at room temperature, the resulting mixture was added to water and extracted with ether. The organic extract was washed twice with water, dried (Na₂SO₄) and concentrated. The crude oil was chromatographed on alumina (100 g) using 10% ethereal hexane as eluant to afford the 3,4,5-trimethoxybenzoate of 2-hydroxy-4-(6-methoxy-2-naphthyl)butane as a pale yellow oil

EXAMPLE 5

S-2-Acetoxy-4-(6-methoxy-2-naphthyl)butane

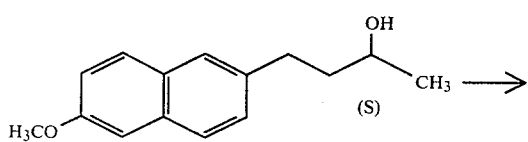 →

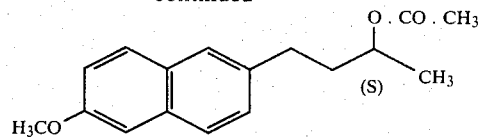

This was prepared in a similar manner to Example 1 using S(+)-4-(6-methoxy-2-naphthyl)-butan-2-ol as starting material.

The colourless oil, which was obtained by chromatography as before, solidified on standing. Recrystallisation of this solid gave S(−)-2-acetoxy-4-(6-methoxy-2-naphthyl)butane, m.p. 41°–3° ; $a_D^{20.0} = -16.2$ (chloroform).

The above compound was active on the rat carageenin test at 45 mg/kg per os.

EXAMPLE 6

S(+)-2-Hydroxy-4-(6-methoxy-2-naphthyl)butane

To a stirred mixture of 6-methoxy-2-naphthaldehyde (9.3 g: 0.05 mole) and 1,3-propanedithiol (5.1 ml: 0.05 mole) in methylene chloride (50 ml) was added dry HCl gas until the solution became saturated.

Stirring was maintained for a further 1 hour and the resulting slurry partitioned between water and methylene chloride. The organic layer was washed successively with water, 1 N potassium hydroxide solution and water, dried (Na₂SO₄) and concentrated. Recrystallisation of the resulting solid from methanol gave 2-(6-methoxy-2-naphthyl)-1,3-dithiane as colourless needles, m.p. 190° (11.7 g: 95%).

To a solution of the latter 9.3 g: 0.038 mole) in tetrahydrofuran (250 ml) at −40° was added dropwise ethereal butyl lithium (25.2 ml of 16 M: 0.038 mole) followed by S(−)-propylene oxide (2.67 ml: 0.038 mole) and the resulting solution then left overnight at room temperature. After acidification with dilute hydrochloric acid the mixture was concentrated and extracted with chloroform. The organic layer was washed with water, dried (Na₂SO₄) and concentrated to give 2-(6-methoxy-2-naphthyl)-2-hydroxypropyl-1,3-dithiane in crude quantitative yield.

This crude dithiane was refluxed for 3 hours with Raney nickel (200 g) in ethanol (500 ml). After filtration through Kieselguhr and concentration the crude product (7.3 g) was chromatographed on alumina (400 g) using chloroform. Recrystallisation of the resulting solid from ether gave S(+)-2-hydroxy-4-(6-methoxy-2- naphthyl)butane, m.p. 94°-5°; $\alpha_D^{26.2} = 12.04°$ (chloroform).

What we claim is:

1. A compound of the formula:

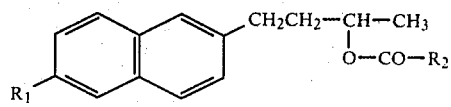

wherein $R_1$ is chloro or methoxy and
$R_2$ is methyl, ethyl, benzyl, 2-methoxyethyl, phenyl, 4-methoxyphenyl or aminomethyl.

2. A compound according to claim 1 wherein $R_2$ is methyl or ethyl.

3. A compound according to claim 1 wherein $R_1$ is chloro.

4. A compound according to claim 1 wherein $R_1$ is methoxy.

5. A compound according to claim 1 wherein $R_1$ is chloro and $R_2$ is methyl.

* * * * *